(12) United States Patent
Velani

(10) Patent No.: US 12,257,212 B2
(45) Date of Patent: Mar. 25, 2025

(54) SMART VIAL INTERACTIVE MEDICATION DOSAGE DISPENSING SYSTEM AND METHOD

(71) Applicant: Laila Velani, Sugar Land, TX (US)

(72) Inventor: Laila Velani, Sugar Land, TX (US)

(*) Notice: Subject to any disclaimer, the term of this patent is extended or adjusted under 35 U.S.C. 154(b) by 0 days.

(21) Appl. No.: 16/387,375

(22) Filed: Apr. 17, 2019

(65) Prior Publication Data
US 2019/0240113 A1   Aug. 8, 2019

Related U.S. Application Data

(63) Continuation of application No. 15/642,433, filed on Jul. 6, 2017, now abandoned.

(51) Int. Cl.
| | |
|---|---|
| *A61J 7/00* | (2006.01) |
| *A61J 1/03* | (2023.01) |
| *A61J 7/04* | (2006.01) |
| *G06V 40/16* | (2022.01) |
| *G16H 10/60* | (2018.01) |
| *G16H 20/13* | (2018.01) |
| *G16H 40/63* | (2018.01) |

(52) U.S. Cl.
CPC ............ *A61J 7/0076* (2013.01); *A61J 1/03* (2013.01); *A61J 7/0418* (2015.05); *A61J 7/0472* (2013.01); *A61J 7/0481* (2013.01); *G16H 20/13* (2018.01); *G16H 40/63* (2018.01); *A61J 7/0445* (2015.05); *A61J 2200/30* (2013.01); *A61J 2200/72* (2013.01); *A61J 2205/50* (2013.01); *G06V 40/161* (2022.01); *G06V 40/172* (2022.01); *G16H 10/60* (2018.01)

(58) Field of Classification Search
CPC .......................... G07F 17/0092; G16H 20/13
USPC ........................................................ 206/225
See application file for complete search history.

(56) References Cited

U.S. PATENT DOCUMENTS

| | | | | |
|---|---|---|---|---|
| 5,954,641 | A * | 9/1999 | Kehr ............... | A61J 7/0481 600/300 |
| 9,345,645 | B1 * | 5/2016 | Chernyak ......... | A61J 7/0084 |
| 2006/0097000 | A1 * | 5/2006 | Gumpert .......... | A61J 7/0481 221/92 |
| 2010/0042430 | A1 * | 2/2010 | Bartfeld .......... | G06F 19/3456 705/2 |
| 2011/0119073 | A1 * | 5/2011 | Hanina ............ | G06K 9/00255 705/2 |
| 2012/0330684 | A1 * | 12/2012 | Jacobs ............ | H04N 23/56 604/404 |
| 2013/0116818 | A1 * | 5/2013 | Hamilton ......... | A61J 7/04 700/236 |

(Continued)

*Primary Examiner* — Timothy R Waggoner
(74) *Attorney, Agent, or Firm* — Baker Botts L.L.P.

(57) ABSTRACT

A medication dispensing system is disclosed, having an interactive vial having a controllable lock for containing medications prescribed for a patient; a processor contained in the vial; a computer program stored in a computer readable medium the computer program comprising instructions for execution by the processor, the computer program comprising: instructions to read patient data for the patient from a data base stored in the computer readable medium; instructions to authorized dispensing of the medication from the vial; and instructions to upon reading an authorization value of "YES", unlock the vial to allow access to the medication from the vial. A method for using the system is disclosed.

8 Claims, 7 Drawing Sheets

(56) References Cited

U.S. PATENT DOCUMENTS

| | | | | |
|---|---|---|---|---|
| 2015/0289805 | A1* | 10/2015 | Eaton | G16H 20/13 |
| | | | | 604/290 |
| 2016/0220180 | A1* | 8/2016 | Fateh | A61M 15/00 |
| 2017/0085756 | A1* | 3/2017 | Thomas | H04N 5/2251 |
| 2018/0333335 | A1* | 11/2018 | Carson | A61J 7/0436 |

* cited by examiner

SMART VIAL INTERACTIVE MEDICATION DOSAGE DISPENSING SYSTEM AND METHOD

BACKGROUND OF THE INVENTION

The current opioid epidemic starts at home by abusing prescribed medications. Typically, a patient abuses medication by taking too many pills too close together ahead of the prescribed medication dosage schedule. In other cases, children access prescription medications and become addicted opioids and turn to street drugs to but illicit drugs. Thus, there is a need for a medication dispensation system and method that controls access by medications at unauthorized times ahead of a medication dosage schedule or by persons other than the patient, such as unauthorized persons such as kids finding the pills in the home medicine cabinet.

FIELD OF THE INVENTION

The present invention relates to the field of controlled medication dispensing.

DETAILED DESCRIPTION

Figure 1:
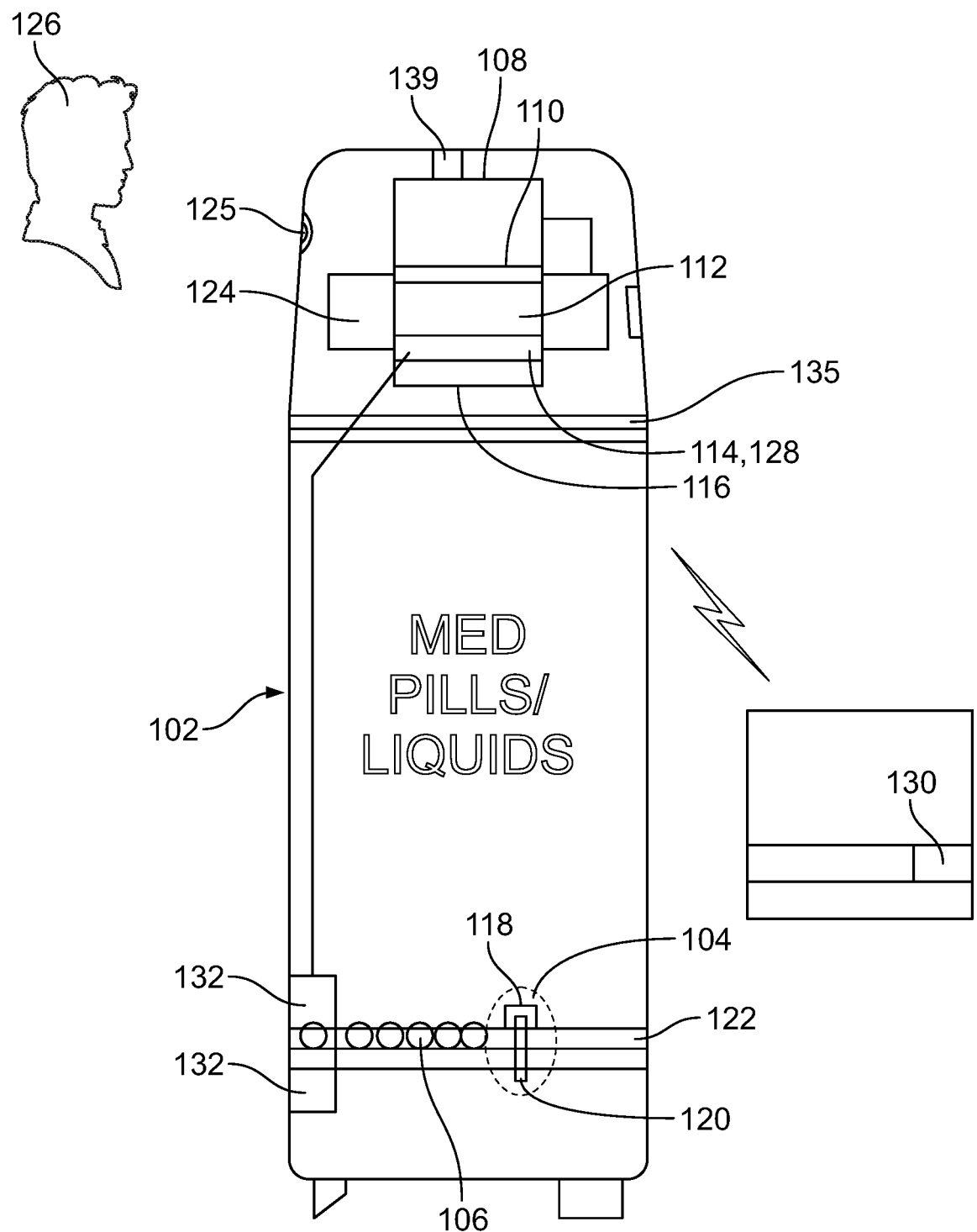
FIG. 1 is block diagram of interactive vial according to one embodiment of the invention.

A Smart Vial interactive medication dosage dispensing system and method, also referred to herein as a "Smart Vial" or "smart vial" is disclosed that dispenses controlled and/or non-controlled medications as prescribed by a licensed medical professional such a physician. In a particular embodiment, the Smart Vial includes but is not limited to a Smart electronic vial for containing and delivering controlled and/or non-control medications as directed by the doctor to a particular patient. An alarm on the digital vial is used to announce delivery of controlled substances and violation of a dosage schedule. A thumb print and/or access code is to release the non-control substances which also uses voice print, iris pattern, gesture, sweat print, double authentication send password to vial, have user speak password and compare to voice print for user. The Smart Vial reduces misuse of medication by kids. The Smart Vial provides a USB digital data port and wireless input output that enables a doctor, pharmacy, emergency medical personnel or patient to access the patient data stored in a data base. A doctor can check the patient data which includes but is not limited to a dispensary report (indicating what medications a patient has taken, dosage and time taken), patient prescription history and/or medication history. In a particular embodiment software is provided comprising computer executable instruction stored on a computer readable medium in data communication with the Smart Vial processor that enables a pharmacy and doctor to fill a medical prescription and to run a dispensary report and to check whether the patient is taking medication on schedule or not. "Data communication" is used herein to mean data is exchanged in both directions between two devices that are in "data communication".

In a particular embodiment, a Wi-Fi device or smart phone is connected to the Smart Vial through which the doctor can get a report of the patient data. The Smart Vial data base contains patient data including but not limited to Patient DL and ID allergy/DOB/Doctor/patient name, age, weight, medical history, food consumption, medication dosage history indication what medications dosages a patient has taken and when (time of day) and pharmacy records. Medications that are stored in the Smart Vial can only be accessed by the patient during the medication time (not before directed medication time). An alert is selectively sent to the provider if the patient is taking overdose, accidentally taking the prescribed medications. The Smart Vial is a reusable and refillable vial. In a particular embodiment, the Smart Vial processor monitors the patient data in the data to calculate a sliding scale drug interaction warning and dosage adjustment based on timing and dosage based on biometric data of patient and timing of dosage. In a particular embodiment, the Smart Vial audibly announces a food warning prior to dosage time, based on a sliding scale calculated by accessing the patient data to indicate what the patient has eaten and what medication the patient has taken. For example, if a patient data indicates the patient has not eaten within 30 minutes of when the dosage is due, the Smart Vial announces that the patient needs to eat and enter the data in the patient data before the dosage is released with a YES command to unlock the vial. If the patient data indicates the patient has eaten within 30 minutes of when the dosage is due, the Smart Vial the dosage is released with a YES command to unlock the vial. If a patient data indicates the patient has not eaten within 30 minutes of when the dosage is due, the Smart Vial announces that the patient needs to eat and enter the data in the patient data before the dosage is released with a YES command to unlock the vial. If the patient data indicates that the dosage requires no food more than 30 minutes before taking, and the medication requires no food to be eaten with the medication, the smart vial announces that the patient should wait to take the medication (also referred to herein as "dosage") for a period of time indicated in the patient data for the medication as indicated in the physician's and pharmacy's data base and sent to the patient data.

In another particular embodiment, the Smart Vial contains a digital camera to take an image of a patient's face to confirm the identity of a patient and also to take an image of a medication being released by the smart vial to confirm the identity of a pill the patient is taking. The pill identity of the pill is confirmed with the patient data base as the pills are placed into the Smart Vial and again as the pill exits the smart vial. The pill is not released by the Smart Vial if the identity of the pill is not confirmed with the patient data on exit from the smart vial. The Smart Vial processor identifies the medication/pills image by comparing the medication image taken by the camera at the Smart Vial to a reference image in the patient data provided by the pharmacy or doctor or medication manufacturer for the prescribed medicine using the shape, color, logo and number on Smart Vial as compared to the reference image in the patient data for the medications prescribed to the patient and contained in the smart vial. If the any one of the shape, color, logo or number on the Smart Vial image of the pill does not match the reference image for prescribed pill, dispensing of the pill is blocked by the Smart Vial processor. The pharmacy and doctor are contacted and are sent the image of the pill being dispensed and the reference image to confirm or override the block on the dispensing of the pill. Errors can occur before the medication is sent to patient in the Smart Vial. An error can occur if the doctor leaves off a critical part of the prescription such as a suffix on a particular medication when calling in a prescription to a pharmacy or the pharmacist may not record the prescription properly leaving off a critical part of the prescription such as a suffix on a particular medication, or a number. Such errors by the doctor or pharmacy can cause the wrong medicine to be loaded into the Smart Vial. Thus, the actual dispensed medicine is imaged by the Smart Vial and checked before dispensing a medication. The pill is identified and compared to the reference image on the Smart Vial to confirm that the type of medication and dosage are verified as proper before dispensing the medication.

In a particular illustrative embodiment, the Smart Vial processor manages and dispenses multiple pills having multiple pill delivery schedules in conjunction with a sliding scale drug interaction and food regiment.

The Smart Vial is made of natural or un-natural material (e.g., plastic, metal). The Smart Vial helps to reduce addiction and overdose and the epidemic on controlled substance abuse. The Smart Vial is useful for doctors, pharmacy, probation officers, court systems to verify whether the patient is taking their prescribed medications on schedule.

In another embodiment, the Smart Vial camera is used to capture video of the patient to monitor and confirm that patient places the imaged pill on their tongue and shows that the pill has been swallowed by the patient by imaging sending a video stream to a Smart Vial server and showing the imaged and dispensed pill on the patient's tongue is no longer visible after being placed on the tongue and drinking water. The Smart Vial helps to continuously track the usage of drugs by the patient.

In a particular illustrative embodiment, the Smart Vial system and method accepts patient authentication data to verify a user's identity. The authentication data includes but is not limited to a patient's iris image captured by the camera for comparison to an iris reference image for the patient, a patient's finger print image captured by the camera for comparison fingerprint reference image, a patient's sweat print captured by the camera for comparison sweat print reference signature, a patient's voice recording captured by the camera for comparison voice print reference which are entered concurrently.

In another embodiment, the Smart Vial generates a password that is spoken by the patient to access the data. The Smart Vial processor accesses the patient data including in the data base, the patient data including but not limited to medical history, age, weight, biometrics for blood pressure, respirations, pulse, blood sugar level, food eaten and when, pills taken, dosage and when and pending dosage schedule. The system and method determines a sliding scale dosage time and quantity and food requirement based on the patient data. The patient data is contained in a medical data base for all patients which can be accessed by police, physicians and emergency personnel when a patient is unconscious or otherwise incapacitated.

The patient can enter additional patient data including but not limited to a pain level to indicate a level of urgency to be taken into account for timing and dosage, for example, in an urgent situation where the pain level is 8 or 9 on a scale of ten, the dosage can be increased with additional pills and the dosage time can be advanced so that the pill is available sooner than the normal dosage schedule if not immediately, or anxiety level to indicate high anxiety. The patient, can enter acute symptoms or and biometric data input into the system processor to determine a sliding scale adjustment to the dosage schedule based on the patient data. The patient also enters foods eaten, quantity of food eaten and the times the foods were eaten as patient data to entering into determining the sliding scale adjustment to the dosage schedule based on the patient data. The system uses the patient data to announce food requirements and prohibitions for the patient.

Turning now to FIG. 1, in a particular illustrative embodiment a medication dispensing system 100 includes but is not limited to an interactive vial 102 having a controllable lock 104 for containing medications 106 prescribed for a patient. A processor 108 is contained in the vial. A computer program 110 stored in a computer readable medium 112 the computer program comprising instructions for execution by the processor, the computer program including but not limited to instructions to read patient data 114 for the patient from a data base 116 stored in the computer readable medium 112, instructions to authorize dispensing of the medication from the vial; and instructions to upon reading an authorization value of "YES", unlock the vial to allow access to the medication from the vial. In a particular illustrative embodiment the controllable lock is a magnetically actuated metal pin 116 and solenoid 118 to magnetically lift the metal pin from a rotatable pill container 120, the instructions to unlock the vial further comprising instructions to send an unlock command to the controllable lock to lift the magnetically actuated pin 116 out of a receiving hole 120 on the rotatable pill container 122 to allow the rotatable pill container to rotate and provide access to a single dosage of the medication from the vial. The computer program further comprises instructions to send a lock command to the lock to release and lower the magnetically actuated pin into the receiving hole 120 on the rotatable pill container 122 to resist further rotation of the rotatable pill container so that only a single dosage of the medication 123 is dispensed.

In a particular embodiment, the system of claim 1, the vial further comprises a patient authentication camera 124 that takes a picture of the patient's face 126; a patient's face reference image 128 stored in patient data 130 for the patient in a database 116. In a particular embodiment, the computer program further comprising instructions to capture and store in the data base an image of the patient's face (picture) 126 on the vial patient authentication camera; instructions to compare the compare the image of the patient's face from the vial camera to the face reference image 128. In another embodiment, the computer program further comprises, instructions to, when the an image of the patient's face on the vial camera and the reference image are compared and correlate above 90, instructions to generate store in the data base a facial recognition authentication result with a value 130 of "YES" indicating a positive result indicating that the vial camera image and the reference image match, else instructions to generate and store in the data base a facial recognition authentication result with a value of "NO" indicating negative result indicating a positive result indicating that the vial camera image and the reference image do not match.

In another particular embodiment, the system further comprises a pair of medication authentication cameras 132 that takes top and bottom pictures (images) 131 of the single dosage of medication 123 in the vial before setting a medical verification value 130 to "YES" indicating that the medication matches a doctor's reference image 140 of the prescribed medication stored in the data base. The doctors reference image is coded at the doctor's office computer which then sends electronically the doctors reference images placed in the patient's data in the data. In another embodiment, the computer program further comprises instructions to compare the compare one or both of the images of the single dose of medication 123 taken by the vial camera, to the medication reference image 140 in the data base and instructions to when the an image of the single dose of medication on the medication authentication camera 132 and the reference image correlate above 90 percent matching, generate and store in the data base a medication authentication result with a value of "YES" indicating a positive result indicating that the vial camera images and the reference image match, else generate and store in the data base a facial recognition authentication result with a value of "NO" indicating negative result indicating a positive result indicating that the vial camera image and the reference image do not match.

In another embodiment, system of further comprises a patient authentication camera that takes a video of the patient's face taking the medication showing the medication on the patient's tongue and then swallowed by the patient and streams the video to the patient data in the data base, in a particular embodiment the database is on a server and the video is streamed to the server.

The data also contains a reference video of the patient's face taking the medication stored in patient data for the patient in a database, the computer program further comprising instructions to compare the video 134 of the patient's face taking the medication to the reference video 136 when the video of image of the patient's face on the vial camera and the reference of the patient's face taking the medication correlate above 90 percent matching, generate store in the data base a medication taken authentication result with a value of "YES" indicating a positive result indicating that the of the patient's face taking the medication and the reference video match and the patient has taken the medication, else generate store in the data base a medication taken authentication result with a value of "NO" indicating a positive result indicating that the of the patient's face taking the medication and the reference video match and the patient has not taken the medication.

In another embodiment, the system further comprises a temperature sensor on the vial, the computer program further comprising instructions to monitor the temperature sensor to determine a vial temperature and store a vial temperature history in the patient data showing vial temperature measurements and the time at which the temperature measurements were made, in one example the temperature is measured once an hour; and instructions to issue an alarm when the vial temperature exceeds 80 degrees Fahrenheit or the vial temperature history exceed a manufacturer's recommendation for storage temperature for the prescribed medication.

In another embodiment, the system further comprises instructions to read patient data from the data base for medications the patient has taken and when; and instructions to calculate, using drug interaction stored in the data base for the medication for the patient, a sliding scale medication dosage schedule based on the food eaten and when and the medications taken and store the sliding scale food requirement value in the data base as an authentication value parameter for calculating the authentication value to unlock the vial.

In another embodiment, the system further comprises instructions to read patient data for food the patient has eaten stored in the patient data as input by the patient or nurse; and instructions to calculate, using doctor food recommendations stored in the data base for the medication for the patient, a sliding scale food requirement value based on food eaten by the patient and when and the medications taken and store the sliding scale food requirement value in the data base as an authentication value parameter for calculating the authentication value to unlock the vial.

In another embodiment, the database is stored in a computer readable medium on the server; the computer program further comprising instructions to determine when a seal 135 on the vial has been breached, instructions to send an alert to authorities when the vial has been breached. A speaker 139 on the vial emits an alarm signal when the vial is open outside of the pharmacy. In another embodiment, the system of the computer program further comprises instructions to sending the unlock command, followed by user setting of delay of 2 to 10 seconds later, at the end of the delay a lock command to resist rotation of the medication wheel. The vial processor send the unlock command to the solenoid that raises the metal pin stopping rotation of the medication wheel.

Figure 2:
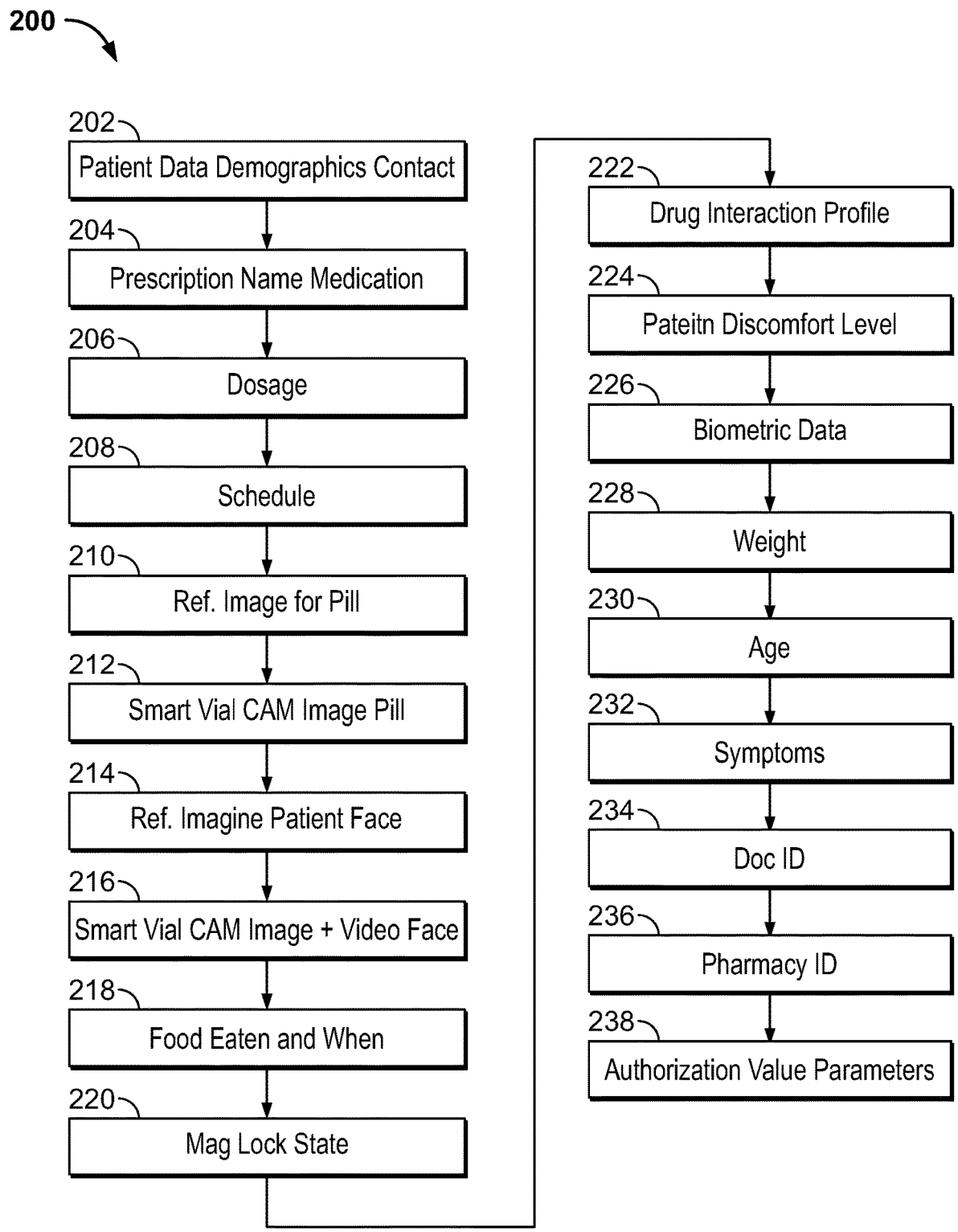
FIG. 2 is diagram of a patient data stored in data structure for used by a processor accessing the data structure in a computer readable medium for controlling dispensing of a prescribed medication.

Turning now to FIG. 2, in a particular illustrative embodiment, a data structure 200 containing patient data 202 used by the vial processor to control dispensing of the medication. As shown in FIG. 2, the data structure includes fields containing patient data accessed and used by the vial processor to control dispensing of the medication. Field 202 contains patient data, prescription name 204, medication dosage 206 and dosage schedule 208, 210 reference images of the top and bottom images of the medication, 212 medication camera top and bottom images, 214 reference images and reference video of patient taking medication, 216 face authentication camera facial image and video of patient taking medication; 218 patient food eaten and when eaten; 220 magnetically actuated lock state: "locked/unlocked". 222 drug interaction profile based on medications taken, when taken and food eaten and when; 224 patient discomfort level; 226 patient biometric data; 228 patient weight; 230 patient age; 232 patient symptoms; 234 prescribing doctor's identification; 236 medication originating pharmacy identification and 238 authorization value parameters. The drug interaction profile for the patient is stored in the data base.

Figure 3:
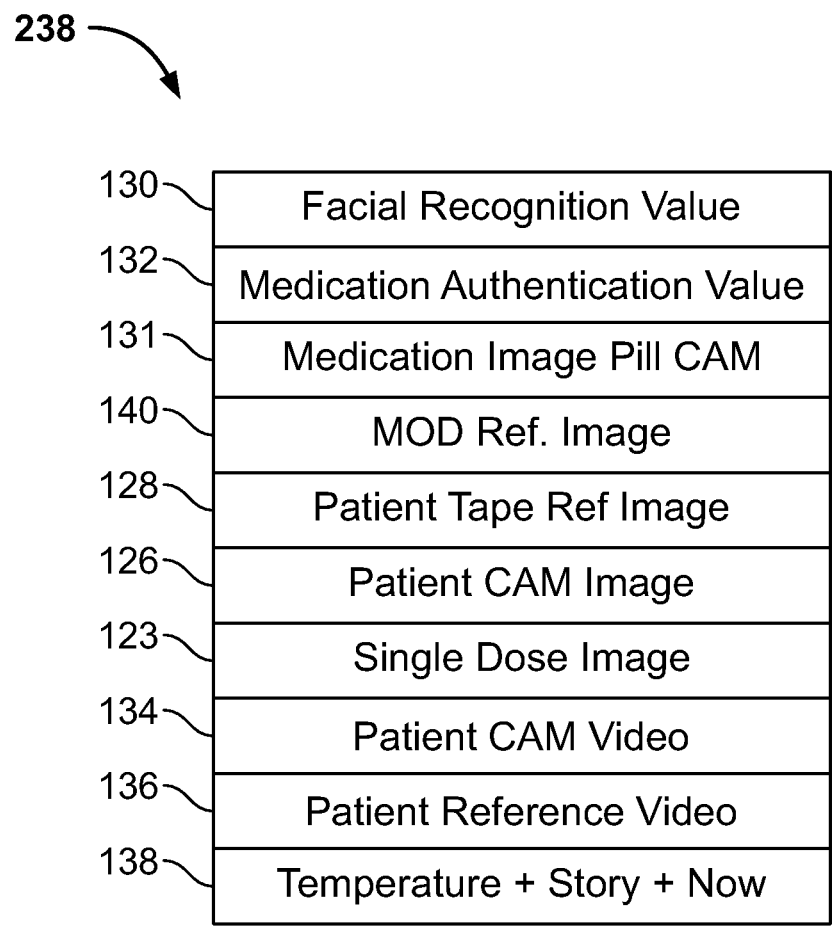
FIG. 3 is diagram of a patient data stored in data structure for used by a processor accessing the data structure in a computer readable medium for controlling dispensing of a prescribed medication.

As shown in FIG. 3 field 238 further comprises facial recognition value 130, medication authorization value 132, 131 medication images of the dosage pill taken from the medication cameras on the vial, 140 medication reference images from doctor; patient face reference image 128; patient authentication camera image 126; single dose images (top and bottom) 123; patient authentication camera video 134; patient reference video 136 and vial temperature and vial temperature history.

Figure 4A:
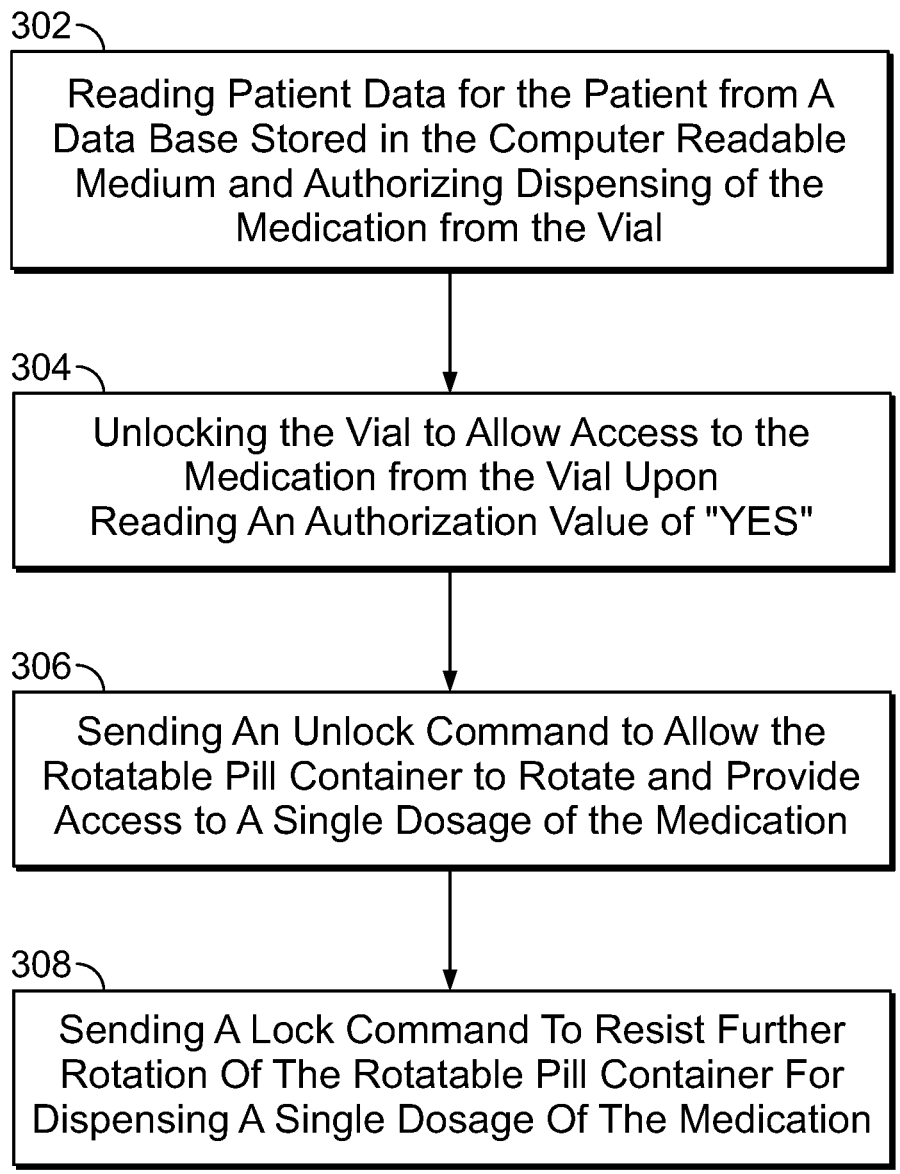
FIG. 4A-4C are flow charts for controlling dispensing of medication.
Figure 4B:
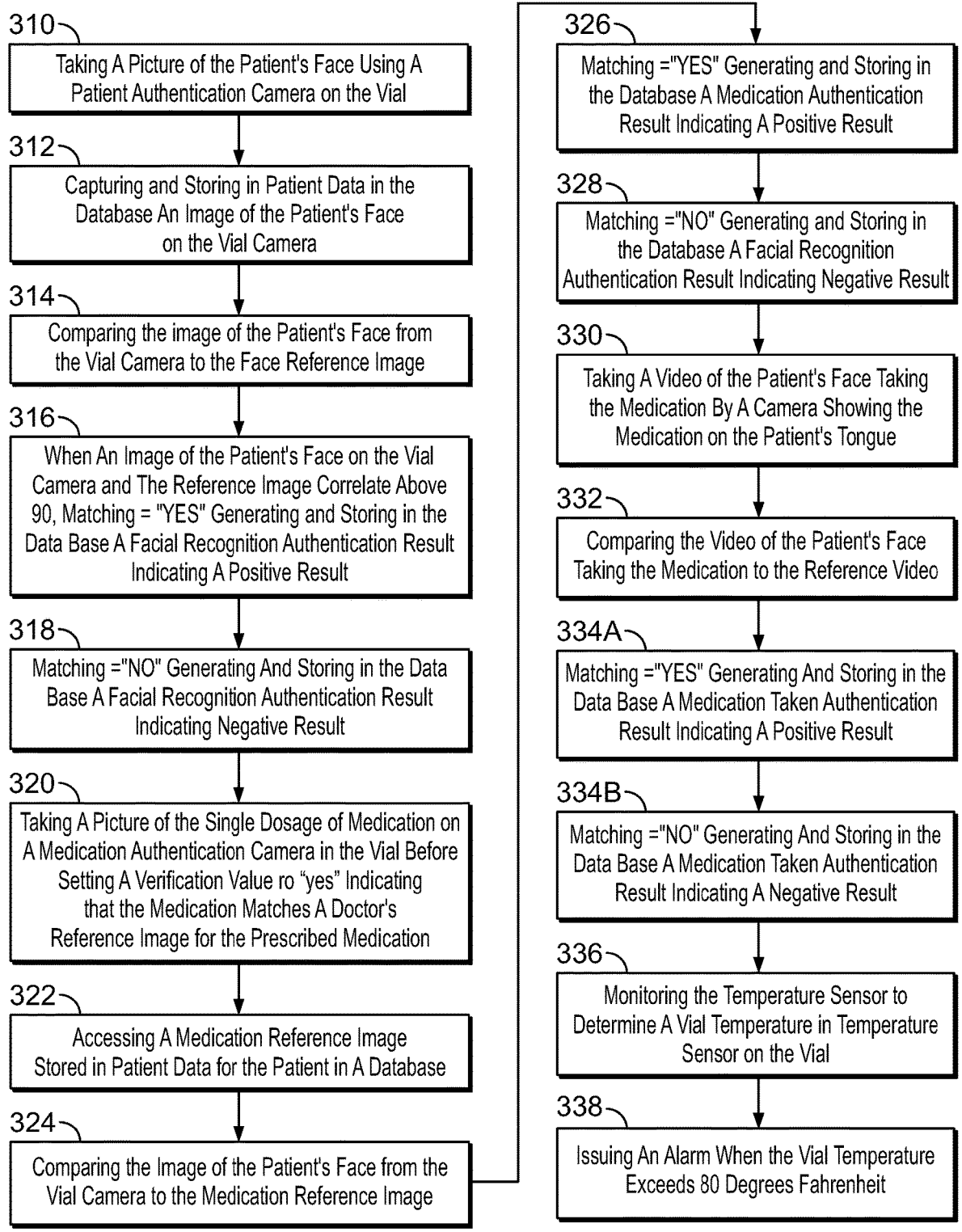
Figure 4C:
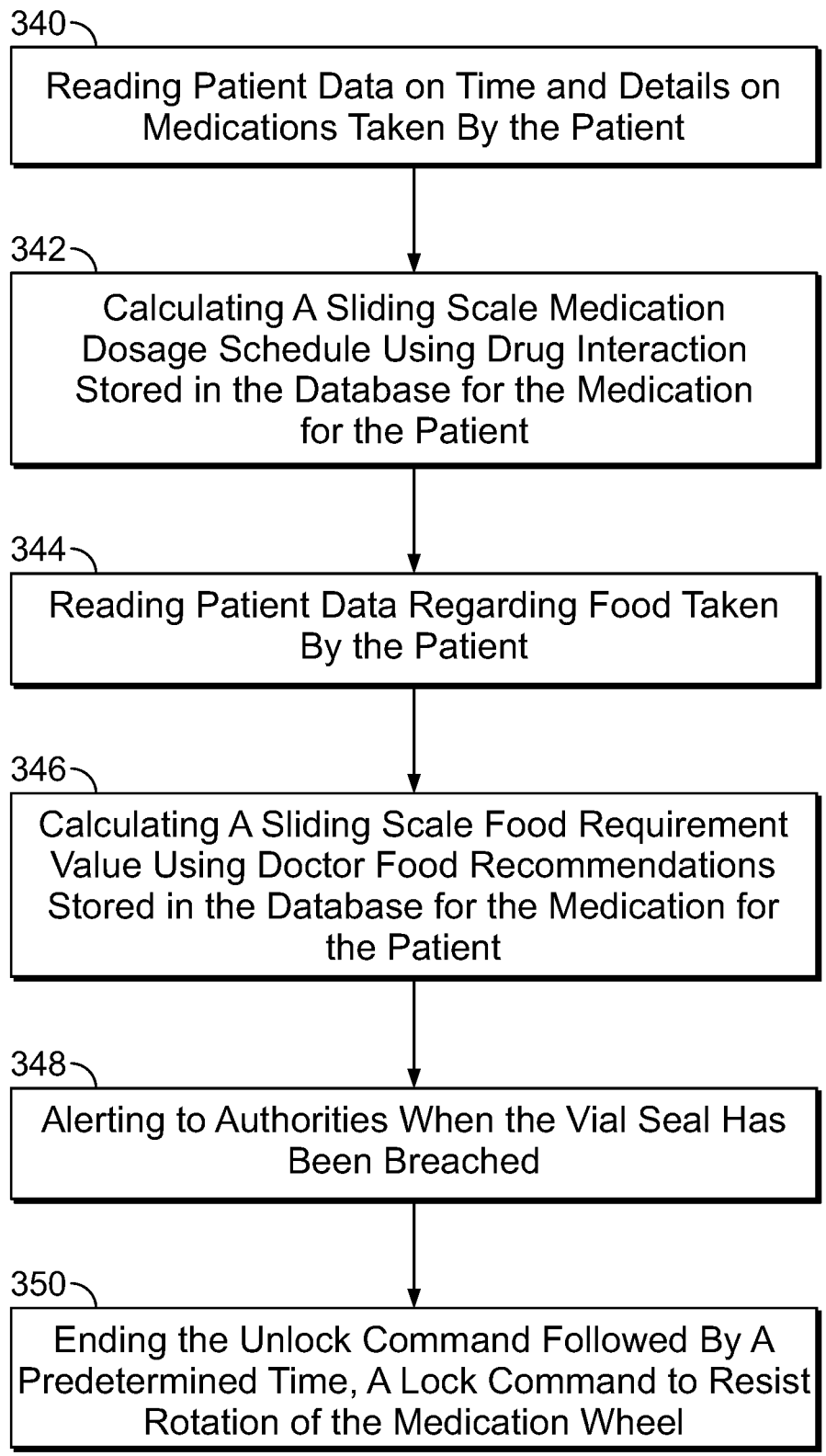

Turning now to FIG. 4, a flow chart for a method dispensing of the medication as shown in FIG. 4, a flow chart showing a method for controlling from a vial processor an interactive vial having a controllable lock for containing medications prescribed for a patient. As shown in FIG. 4, the method starts at 302 reading patient data for the patient from a data base stored in the computer readable medium; 302 authorizing dispensing of the medication from the vial; and 304 upon reading an authorization value of "YES", unlocking the vial to allow access to the medication from the vial. The method proceeds to 306 sending an unlock command to the controllable lock to lift a magnetically actuated pin out of a receiving hole on the rotatable pill container to allow the rotatable pill container to rotate and provide access to a single dosage of the medication and 308 sending a lock command to the lock to release and lower the magnetically actuated pin into a receiving hole on the rotatable pill container to resist further rotation of the rotatable pill container so that only a single dosage of the medication is dispensed.

In another embodiment the method further comprises 310 taking a picture of the patient's face using a patient authentication camera on the vial; 312 capturing and storing in patient data in the data base an image of the patient's face on the vial camera; and 314 comparing the compare the image of the patient's face from the vial camera to the face reference image; and 316 when the an image of the patient's face on the vial camera and the reference image correlate above 90 percent matching, generating and storing in the data base a facial recognition authentication result with a value of "YES" indicating a positive result indicating that the vial camera image and the reference image match, else 318 generating and storing in the data base a facial recognition authentication result with a value of "NO" indicating negative result indicating a positive result indicating that the vial camera image and the reference image do not match.

In another embodiment the method further comprises 320 taking a picture of the single dosage of medication on a medication authentication camera in the vial before setting a verification value to "YES" indicating that the medication matches a doctor's reference image for the prescribed medication; 322 accessing a medication reference image stored in patient data for the patient in a database; 324 comparing the image of the patient's face from the vial camera to the medication reference image; 326 generating and storing in the data base a medication authentication result with a value of "YES" indicating a positive result indicating that the medication authentication camera image and the medication reference image match when the an image of the patient's face on the vial camera and the reference image correlate above 90; else 328 generating and storing in the data base a facial recognition authentication result with a value of "NO" indicating negative result indicating a positive result indicating that the vial camera image and the reference image do not match. In another embodiment the "YES" and "NO" commands are markers inserted into an authentication data stream sent to the vial processor. A YES marker comprises two YES markers comprising a data value of 1 are sent 100 milliseconds apart from each other which are acknowledged by the vial processor, followed by two second additional YES markers comprising a data value of 2 are sent to the vial processor separated by 200 milliseconds after vial processor acknowledges the first two YES markers. If the timing or data value varies for either the first two YES markers or the second two YES markers, the YES command sequence is ignored by the vial processor.

A NO marker comprises two NO markers comprising a data value of 3 are sent 50 milliseconds apart from each other which are acknowledged by the vial processor, followed by two second additional NO markers comprising a data value of 4 are sent to the vial processor separated by 250 milliseconds after vial processor acknowledges the first two NO markers. If the timing or data value varies for either the first two NO markers or the second two NO markers, the NO command sequence is ignored by the vial processor.

In another embodiment the method further comprises 330 taking a video on the patient authentication camera, of the patient's face taking the medication showing the medication on the patient's tongue and then swallowed; 332 comparing the video of the patient's face taking the medication to the reference video when the video of image of the patient's face on the vial camera and the reference video of the patient's face taking the medication correlate above 90, 334 generating and storing in the data base a medication taken authentication result with a value of "YES" indicating a positive result indicating that the of the patient's face taking the medication and the reference video match and the patient has taken the medication, else generating and storing in the data base a medication taken authentication result with a value of "NO" indicating a positive result indicating that the of the patient's face taking the medication and the reference video match and the patient has not taken the medication. The method further proceeds to 336 monitoring the temperature sensor to determine a vial temperature a temperature sensor on the vial; and 338 issuing an alarm when the vial temperature exceeds an alarm temperature of 80 degrees Fahrenheit. The alarm temperature is programmable and is stored in the physician's data base and pharmacy's data based and is down loaded to memory accessed by the vial processor. The vial processor issues and alarm when the vial temperature exceeds the alarm temperature for a duration specified in the database and down loaded to memory accessed by the vial processor.

In another embodiment, the method further comprises 340 reading patient data for medications the patient has taken and when the medications were taken; and 342 calculating, using drug interaction stored in the data base for the medication for the patient, a sliding scale medication dosage schedule based on the food eaten and when and the medications were taken and store the sliding scale food requirement value in the data base as an authentication value parameter for calculating the authentication value to unlock the vial.

In another embodiment, the method further comprises 344 reading patient data for food the patient has eaten; and 346 calculating, using doctor food recommendations stored in the data base for the medication for the patient, a sliding scale food requirement value based on food eaten and when and the medications taken and store the sliding scale food requirement value in the data base as an authentication value parameter for calculating the authentication value to unlock the vial. In another embodiment, the vial processor uses the sliding scale food requirement to determine and announce at the vial as an alert to the patient taking the medication that they need to eat while taking the medication.

In another embodiment, the method further comprises 348 alerting to authorities when the vial seal has been breached. In another embodiment, the method further comprises 350 ending the unlock command followed by 2 seconds later, a lock command to resist rotation of the medication wheel.

Figure 5:
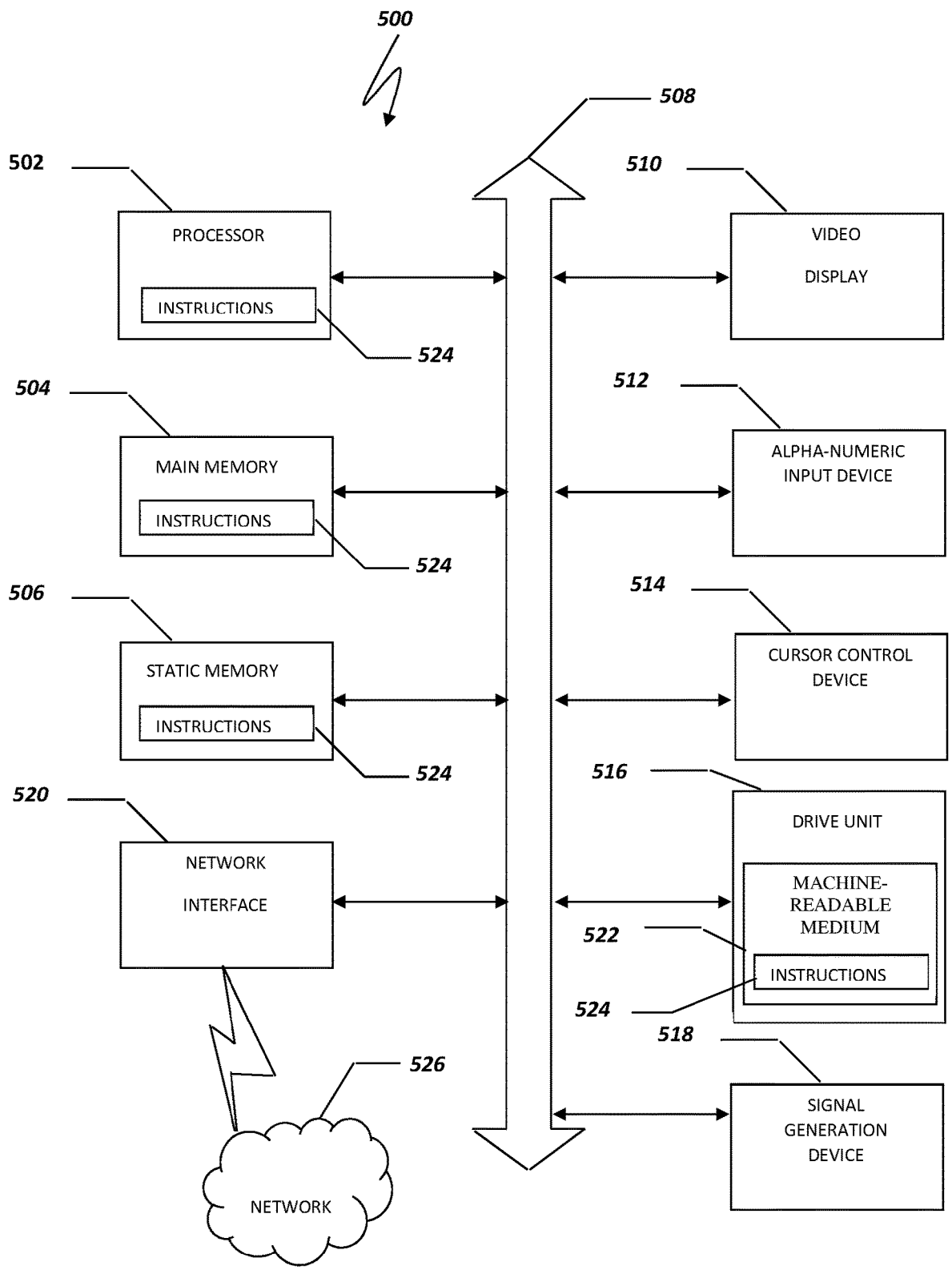
FIG. 5 is general diagram of a computer system for use in a particular embodiment of the invention.

FIG. 5 is a diagrammatic representation of a machine in the form of a computer system 500 within which a set of instructions, when executed, may cause the machine to perform any one or more of the methodologies discussed herein. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment. The machine may comprise a server computer, a client user computer, a personal computer (PC), a tablet PC, a set-top box (STB), a Personal Digital Assistant (PDA), a cellular telephone, a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any machine capable of executing a set of instructions (sequential or otherwise) that specify actions to be taken by that machine.

It will be understood that a device of the present invention includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The Smart Vial includes but is not limited to a computer system 500 may include a Smart Vial processor 502 (e.g., a central processing unit (CPU), a graphics processing unit (GPU), or both), a main memory 504 and a static memory 506, which communicate with each other via a bus 508. The computer system 500 may further include a video display unit 510 (e.g., liquid crystals display (LCD), a flat panel, a solid-state display, or a cathode ray tube (CRT)). The computer system 500 may include an input device 512 (e.g., a keyboard), a cursor control device 514 (e.g., a mouse), a disk drive unit 516, a signal generation device 518 (e.g., a speaker or remote control) and a network interface.

The disk drive unit 516 may include a machine-readable medium 522 on which is stored one or more sets of instructions (e.g., software 524) embodying any one or more of the methodologies or functions described herein, including those methods illustrated in herein above. The instructions 524 may also reside, completely or at least partially, within the main memory 504, the static memory 506, and/or within the processor 502 during execution thereof by the computer system 500. The main memory 504 and the processor 502 also may constitute machine-readable media. Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present invention, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

As shown in FIG. 5, the present invention contemplates a machine-readable medium containing instructions 524, or that which receives and executes instructions 524 from a propagated signal so that a device connected to a network environment 526 can send or receive voice, video or data, and to communicate over the network 526 using the instructions 524. The instructions 524 may further be transmitted or received over a network 526 via the network interface device 520. The machine-readable medium may also contain a data structure for containing data useful in providing a functional relationship between the data and a machine or computer in an illustrative embodiment of the disclosed system and method.

While the machine-readable medium 522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape embodying computer instructions in a transmission medium; and/or a digital file attachment to e-mail or other self-contained information archive or set of archives is considered a distribution medium equivalent to a tangible storage medium. Accordingly, the invention is considered to include any one or more of a tangible machine-readable medium or a tangible distribution medium, as listed herein and including art-recognized equivalents and successor media, in which the software implementations herein are stored.

Although the present specification describes components and functions implemented in the embodiments with reference to particular standards and protocols, the invention is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A medication dispensing system, the system comprising:
   an interactive vial comprising:
      a controllable lock for containing medications prescribed for a patient, wherein the controllable lock comprises a pin and a solenoid, wherein the solenoid is configured to magnetically lift the pin from a receiving hole upon receiving an authorized fingerprint from the patient;
      a patient authentication camera configured to take a video of the patient's face taking the medication showing the medication on the patient's tongue and swallowed, wherein the video is stored in patient data for the patient in a database as a reference video; and
      a temperature sensor configured to measure a temperature of the interactive vial, wherein the interactive vial is configured to issue an alarm if the temperature of the interactive vial exceeds a threshold;
   a processor contained in the vial and operable to be communicatively coupled to an external device to transmit a log of medication data associated with the patient;
   a computer program stored in a computer readable medium the computer program comprising instructions for execution by the processor, the computer program comprising:
      instructions to read patient data for the patient from a data base stored in the computer readable medium;
      instructions to read a dispensary report in the patient data to determine whether the patient is on schedule with dosage and time taken;
      instructions to determine a sliding scale adjustment to a dosage schedule based on the dispensary report; and
      instructions to authorize dispensing of the medication from the vial upon receiving an authorization value of "YES", unlock the vial to allow access to the medication from the vial, wherein the authorization value is indicated in a data stream containing markers sent to the smart vial; and
   a pair of medication authentication cameras coupled to the vial that take a picture of a front side and a back side of the single dosage of medication in the vial and comparing the front side and back side pictures to reference images for the medication shape, color and logo, and number on the pictures before setting a verification value to "YES" indicating that the medication matches a doctor's reference image for the prescribed medication.

2. The system of claim 1, further comprising:
   the patient authentication camera that takes a picture of the patient's face;
   a patient's face reference image stored in patient data for the patient in a database;
   the computer program further comprising:
      instructions to capture and store in the data base an image of the patient's face on the vial camera, wherein at least a portion of the image includes the patient's iris;
      instructions to compare the image of the patient's face from the vial camera to the face reference image, wherein at least a portion of the reference image includes the patient's iris; and
      instructions to generate and store in the data base a facial recognition authentication result with a value of "YES" indicating a positive result indicating that the vial camera image and the reference image match when the image of the patient's face on the vial camera and the reference image correlate above 90 percent matching, else generate and store in the data base a facial recognition authentication result with a value of "NO" indicating negative result indicating a positive result indicating that the vial camera image and the reference image do not match.

3. The system of claim 1, further comprising:
   the patient's face reference image stored in patient data for the patient in a database;
   the computer program further comprising:
      instructions to capture and store in the data base an image of the patient's face on the vial camera, wherein at least a portion of the image includes the patient's iris;
      instructions to compare the compare the image of the patient's face from the vial camera to the face reference image, wherein at least a portion of the reference image includes the patient's iris; and
      instructions to generate and store in the data base a facial recognition authentication result with a value of "YES" indicating a positive result indicating that the vial camera image and the reference image match when the image of the patient's face on the vial camera and the reference image correlate above 90, else generate and store in the data base a facial recognition authentication result with a value of "NO" indicating negative result indicating a positive result indicating that the vial camera image and the reference image do not match.

4. The system of claim 1, further comprising:
   the computer program further comprising:
      instructions to compare the video of the patient's face taking the medication to the reference video when the video of image of the patient's face on the vial camera and the reference of the patient's face taking, the medication correlate above 90, generate store in the data base a medication taken authentication result with a value of "YES" indicating a positive result; and
      indicating that the of the patient's face taking the medication and the reference video match and the patient has taken the medication, else generate store in the data base a medication taken authentication result with a value of "NO" indicating a positive result indicating that the of the patient's face taking the medication and the reference video match and the patient has not taken the medication.

5. A medication dispensing system, the system comprising:
an interactive vial comprising:
a controllable lock for containing medications prescribed for a patient, wherein the controllable lock comprises a pin and a solenoid, wherein the solenoid is configured to magnetically lift the pin from a receiving hole upon receiving an authorized fingerprint from the patient; and
a patient authentication camera configured to take a video of the patient's face taking the medication showing the medication on the patient's tongue and swallowed, wherein the video is stored in patient data for the patient in a database as a reference video;
a processor contained in the vial and operable to be communicatively coupled to an external device to transmit a log of medication data associated with the patient;
a computer program stored in a computer readable medium the computer program comprising instructions for execution by the processor, the computer program comprising:
instructions to read patient data for the patient from a data base stored in the computer readable medium; and
instructions to authorize dispensing of the medication from the vial upon receiving an authorization value of "YES", unlock the vial to allow access to the medication from the vial, wherein the authorization value is indicated in a data stream containing markers sent to the smart vial; and
a pair of medication authentication cameras coupled to the vial that take a picture of a front side and a back side of the single dosage of medication in the vial and comparing the front side and back side pictures to reference images for the medication shape, color and logo, and number on the pictures before setting a verification value to "YES" indicating that the medication matches a doctor's reference image for the prescribed medication.

6. The medication dispensing system of claim 5, wherein the interactive vial comprises a temperature sensor configured to measure a temperature of the interactive vial, wherein the interactive vial is configured to issue an alarm if the temperature of the interactive vial exceeds a threshold.

7. A medication dispensing system, the system comprising:
an interactive vial comprising:
a controllable lock for containing medications prescribed for a patient, wherein the controllable lock comprises a pin and a solenoid, wherein the solenoid is configured to magnetically lift the pin from a receiving hole upon receiving an authorized fingerprint from the patient; and
a patient authentication camera configured to take a video of the patient's face taking the medication showing the medication on the patient's tongue and swallowed, wherein the video is stored in patient data for the patient in a database as a reference video;
a processor contained in the vial and operable to be communicatively coupled to an external device to transmit a log of medication data associated with the patient; and
a computer program stored in a computer readable medium the computer program comprising instructions for execution by the processor, the computer program comprising:
instructions to read patient data for the patient from a data base stored in the computer readable medium;
instructions to read a dispensary report in the patient data to determine whether the patient is on schedule with dosage and time taken;
instructions to determine a sliding scale adjustment to a dosage schedule based on the dispensary report; and
instructions to authorize dispensing of the medication from the vial upon receiving an authorization value of "YES", unlock the vial to allow access to the medication from the vial, wherein the authorization value is indicated in a data stream containing markers sent to the smart vial.

8. The medication dispensing system of claim 7, wherein the interactive vial comprises a temperature sensor configured to measure a temperature of the interactive vial, wherein the interactive vial is configured to issue an alarm if the temperature of the interactive vial exceeds a threshold.

* * * * *